(12) United States Patent
Bani-Hashemi (10) Patent No.: US 7,355,682 B2
(45) Date of Patent: Apr. 8, 2008

(54) REMOTE CENTER RANGE FINDER

(75) Inventor: Ali Bani-Hashemi, Walnut Creek, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 368 days.

(21) Appl. No.: 11/030,836

(22) Filed: Jan. 7, 2005

(65) Prior Publication Data

US 2006/0152704 A1    Jul. 13, 2006

(51) Int. Cl.
*G00C 3/00* (2006.01)
(52) U.S. Cl. .................................................. 356/3.1
(58) Field of Classification Search .................. 356/3.1
See application file for complete search history.

(56) References Cited

U.S. PATENT DOCUMENTS 4,731,853 A * 3/1988 Hata et al. .................. 356/603
5,461,478 A * 10/1995 Sakakibara et al. ......... 356/623
6,088,106 A   7/2000 Röckseisen ................. 356/375

* cited by examiner

*Primary Examiner*—Thomas H. Tarcza
*Assistant Examiner*—Luke D. Ratcliffe (57) ABSTRACT

A system for measuring the distance from a first point spaced away from a surface of an object to a second point on a surface of the object along an axis extending through the first and second points includes one or more light projection assemblies for projecting light stripes onto the surface of the object so that the light stripes pass though the second point. An imaging device detects the position of the second point by sensing the light stripes at the second point. A distance calculator may then calculate the distance between the first point and the second point using the position of the second point detected by the imaging device. The system is calibrated using the cross-ratio of points detected along the axis by the imaging device.

16 Claims, 6 Drawing Sheets

REMOTE CENTER RANGE FINDER

BACKGROUND OF THE INVENTION

The present invention relates generally to apparatus and methods for measuring the distance between two points, and particularly, to a system and method for measuring the distance from a first point spaced away from a surface of an object to a second point on a surface of an object. More specifically, the present invention relates to a remote center range finder suitable for use in radiation oncology for measuring the distance of a radiation source to the body of a patient (i.e., source-to-skin-distance) during radiation treatment.

Radiation oncology uses radiation therapy for the treatment of cancerous tumors in a patient's body. Conventional radiation therapy employs a linear accelerator or LINAC, which directs a beam of radiation (e.g., gamma ray or X-ray radiation) toward a cancerous tumor in a patient to deliver a predetermined dose of therapeutic radiation to the tumor. Unfortunately, healthy tissue and organs are often in the path of a radiation beam during radiation treatment, and may be damaged by the radiation. Therefore, it is desirable to minimize the amount of radiation delivered to healthy tissue surrounding the cancerous tumor during the course of radiation therapy.

One method for minimizing damage to healthy tissue and organs during radiation treatment is to determine the distance between the radiation source and the patient's skin along the principle axis of the radiation treatment device (i.e., along the imaginary line connecting the radiation source to the machine isocenter). This distance is typically referred to as the source-to-skin distance (SSD). Accurately measuring SSD helps ensure the radiation beam is substantially directed at the cancerous tumor's center. Accordingly, small variations in SSD measurement may cause significant variations in the radiation treatment dose to the tumor.

Current treatment plans are designed under the assumption that SSD measurement errors may occur that result in misdelivery of radiation. Treatment plans compensate for this potential misdelivery by specifying lower doses or smaller beam shapes (e.g., beams that do not radiate the edges of a tumor) than would be specified if misdelivery was not expected. Such compensation can be decreased as margins of error in SSD measurements are decreased. Consequently, improving the accuracy of SSD measurements may allow for the use of more aggressive treatments. Specifically, if the margin of error in SSD measurement is known to be very small, treatments may be designed to safely radiate a greater portion of a tumor with higher doses than would be possible where the margin of error is larger.

Treatment apparatus used in radiation oncology are typically equipped with an optical range finder that enables the user to read SSD during patient setup. For example, it is known to project a scale onto the skin surface of the patient by means of a projector. The scale is in the form of a graduated line projected onto the scene. This line must include the axis along which the distance measurement is desired, i.e. the axis connecting the first and second points. Two additional planes of light project two light stripes onto the scene. Each plane of light contains the axis. In short, three planes (one containing the scale, and two planes of light) are projected, and these planes intersect at the principle axis of the system. Numerical values applied to the scale indicate the distance of the skin surface from the focus in the intersection reticle of the light-beam localizer projected onto the skin surface. However, these devices do not directly measure SSD and may not be accurate. As a result, it is desirable to have a system and apparatus that directly measures SSD, thereby improving accuracy and precision of SSD measurements.

SUMMARY OF THE INVENTION

The present invention is directed to a system and method for measuring the distance between a first point spaced away from a surface of an object and a second point on a surface of an object along an axis extending through the first point and the second point. The system and method are particularly suitable for use in radiation oncology for measuring the distance of a radiation source to the body of a patient (e.g., the source-to-skin-distance (SSD)) during radiation treatment. The present invention is further directed to a method for efficiently calibrating such distance measuring systems so that highly accurate distance measurements may be obtained.

In one specific embodiment, the present invention provides a system for measuring the distance from a first point spaced away from a surface of an object to a second point on a surface of an object along an axis extending through the first point and the second point. The system includes two or more projection assemblies for projecting planes of light that intersect the surface of the object to form light stripes on the surface which intersect at the second point. Each of these planes of light pass through (i.e. include) the axis connecting the first and second points. An imaging device detects the position of the second point by sensing the intersection of the light stripes at the second point. A distance calculator may then calculate the distance between the first point and the second point using the position of the second point detected by the imaging device.

In a second specific embodiment, the present invention provides a system for measuring the distance from a first point spaced away from a surface of an object to a second point on a surface of an object along an axis passing through the first and second points. The system includes a projection assembly for projecting a plane of light onto the surface of the object so that the plane of light intersects the surface to form a light stripe on the surface. The plane of light projected by the projection assembly contains the axis so that the light stripe passes though the second point. An imaging device having a sensor oriented for sensing light reflected from points on the object along a line coplanar with the first point, the second point and the focal point of the imaging device detects the position of the second point by sensing the light stripe at the second point. The imaging device further detects the position of a third point at a predetermined distance from the first point along the axis. A distance calculator may then calculate the distance between the first point and the second point using the position of the second point detected by the imaging device. The distance calculator determines the distance between the second point and the third point and subtracts the distance between the second point and the third point from the distance between the first point and the third point for determining the distance between the first point and the second point.

In a third specific embodiment, the present invention provides a radiation treatment device for providing therapeutic radiation treatment to a patient. The radiation treatment device includes a radiation source for projecting a beam of radiation onto the body of a patient being treated and a range finder for measuring the distance from the radiation source to a second point on the surface of the body of the patient. The range finder includes two or more projection assemblies for projecting planes of light that intersect the surface of the object to form light stripes on the surface which intersect at the second point. The planes of light also include the source, therefore their intersection contains the line connecting the source to the second point of the surface. An imaging device detects the position of the second point by sensing the intersection of the light stripes at the second point. A distance calculator may then calculate the distance between the first point and the second point using the position of the second point detected by the imaging device.

In a fourth specific embodiment, the present invention provides a radiation treatment device for providing therapeutic radiation treatment to a patient. The radiation treatment device includes a radiation source for projecting a beam of radiation onto the body of a patient being treated and a range finder for measuring the distance from the radiation source to a second point on the surface of the body of the patient. The range finder includes a projection assembly for projecting a plane of light onto the surface of the object so that the plane of light intersects the surface to form a light stripe on the surface. The plane of light projected by the projection assembly contains the axis so that the light stripe passes though the second point. An imaging device having a sensor oriented for sensing light reflected from points on the object along a line coplanar with the first point, the second point and the focal point of the imaging device detects the position of the second point by sensing the light stripe at the second point. The imaging device further detects the position of a third point at a predetermined distance from the first point along the axis. A distance calculator may then calculate the distance between the first point and the second point using the position of the second point detected by the imaging device. The distance calculator determines the distance between the second point and the third point and subtracts the distance between the second point and the third point from the distance between the first point and the third point for determining the distance between the first point and the second point.

In a fifth specific embodiment, the present invention provides a method for measuring the distance from a first point spaced away from a surface of an object to a second point on a surface of an object along an axis extending through the first point and the second point. The method comprises the steps of projecting a first plane of light so that the first plane of light passing through the first point intersects the surface of the object to form a first light stripe on the surface; projecting a second plane of light passing through the first point so that the second plane of light intersects the surface of the object to form a second light stripe on the surface, the first light stripe intersecting the second light stripe at the second point (the constraint that the two planes pass through the first point ensures that the second point is measured along the axis connecting the first and second points); and detecting the position of the second point by sensing the intersection of the first light stripe and the second light stripe at the second point, the distance between the first point and the second point being determined from the detected position of the second point.

In a sixth specific embodiment, the present invention provides a method for measuring the distance from a first point spaced away from a surface of an object to a second point on a surface of an object along an axis extending through the first point and the second point. The method includes the steps of projecting a plane of light onto the surface of the object so that the plane of light intersects the surface to form a light stripe on the surface, wherein the plane of light contains the axis so that the light stripe passes though the second point; detecting the position of the second point by sensing the light stripe at the second point via an imaging device, wherein the imaging device includes a sensor oriented for sensing light reflected from points on the object along a line coplanar with the first point, the second point and the focal point of the imaging device; defining a third point along a line extending through the first point and the second point, wherein the distance between the first point and the third point is predetermined; determining the distance between the second point and the third point; and subtracting the distance between the second point and the third point from the distance between the first point and the third point for determining the distance between the first point and the second point.

The methods may be implemented as computer-executable instructions stored in a computer-readable medium and may be executed by a computer, the control system of a radiation treatment device such as a linear accelerator (LINAC), a range finder system, or the like.

It is to be understood that both the foregoing general description and the following detailed description are exemplary and explanatory only and are not necessarily restrictive of the invention claimed. The accompanying drawings, which are incorporated in and constitute a part of the specification, illustrate embodiments of the invention and together with the general description, serve to explain the principles of the invention.

DETAILED DESCRIPTION OF SPECIFIC EMBODIMENTS

Reference will now be made in detail to the presently preferred embodiments of the invention, examples of which are illustrated in the accompanying drawings.

Figure 1:
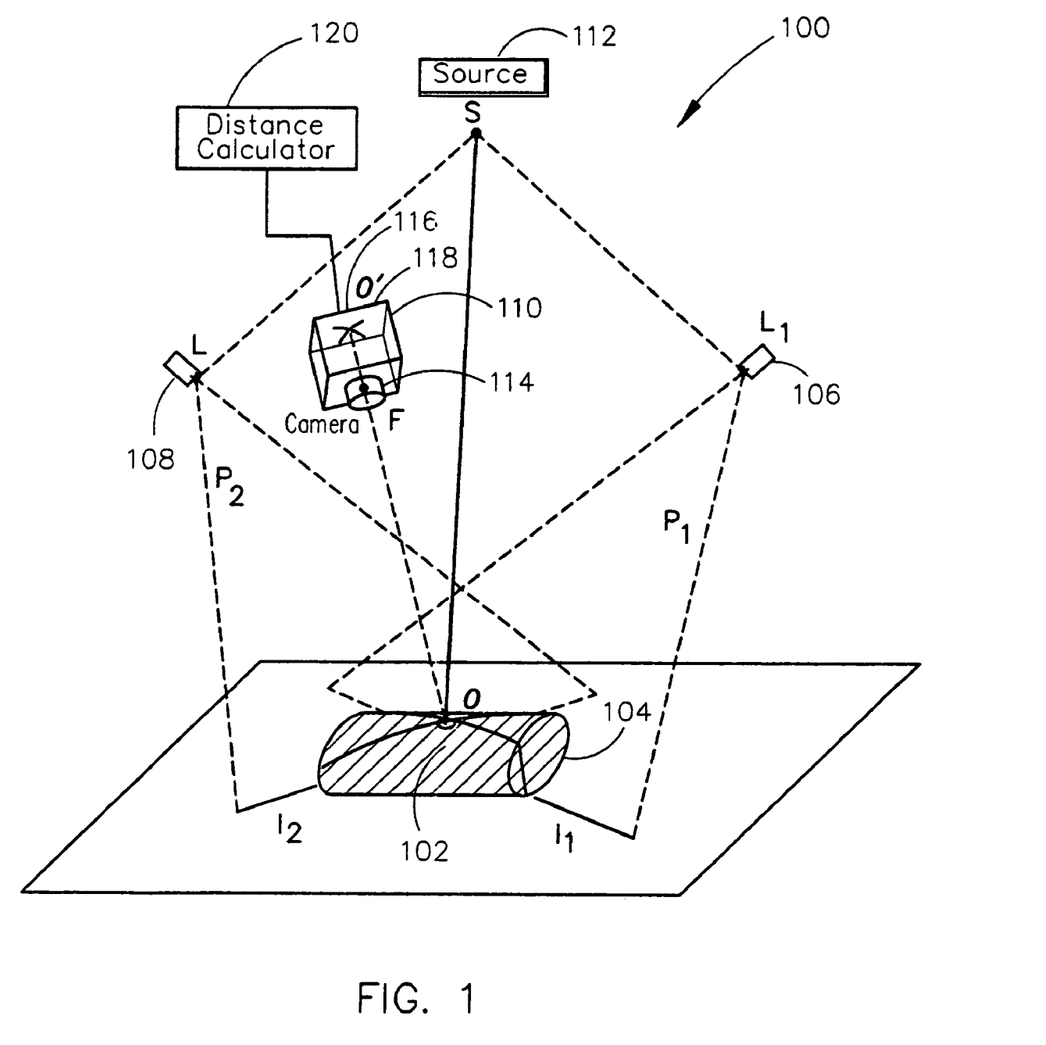
FIG. 1 is a block diagram illustrating a system for measuring the distance from a first point spaced away from a surface of the object to a second point on a surface of an object in accordance with an exemplary embodiment of the present invention.

FIG. 1 illustrates a system 100 for measuring the distance from a first point S spaced away from a surface 102 of an object 104 to a second point O on the surface 102 of the object 104 such that second point O is on a principle axis originating from the point S in accordance with the present invention. As shown in FIG. 1, the system 100 includes two or more projection assemblies 106 and 108 which project planes of light that intersect the surface 102 of the object 104 to form light stripes on the surface 102. An imaging device 110 detects the position of the second point O by sensing the intersection of the light stripes at the second point O. The distance between the first point S and the second point O may then be determined from the detected position of the second point O.

In the specific embodiment shown in FIG. 1, the system 100 includes a first projection assembly 106 for projecting a first plane of light so that the first plane of light intersects the surface 102 to form a first light stripe on the surface 102 and a second projection assembly 108 for projecting a second plane of light so that the second plane of light intersects the surface 102 to form a second light stripe on the surface 102. The two planes of light intersect along an axis that included the first point, point S. The first projection assembly 106 and the second projection assembly 108 are oriented so that the first light stripe intersects the second light stripe creating a point of light projected onto the surface 102 at point O. In exemplary embodiments, the point of light, at point O, may be made to appear to emanate from the first point, point S.

The projection assemblies 106 and 108 may comprise light stripe projectors using known light projection technologies. For example, in exemplary embodiments, the projection assemblies 106 and 108 may include a conventional light source coupled with a lens/mask system for projecting light in a plane. Laser or laser diode-based projection technologies may also be utilized. Light projected by the projection assemblies 106 and 108 may be visible or invisible to the human eye (e.g., the light may have a wavelength in the visible range or may be ultraviolet, infrared, or the like) without departing from the scope and intent of the present invention.

As shown in FIG. 1, the line SO represents the principle axis of the system 100, where point S is the first point (e.g., the location of the radiation source 112 of a radiation treatment device, or the like) and point O is the second point representing the intersection of the principle axis SO with the surface 102 of the object 104. The first projection assembly 106 projects a plane of light onto the object from a point $L_1$ resulting in the light stripe $l_1$ being projected onto the surface 102. The light stripe $l_1$ is thus formed by the intersection of the plane of light $P_1$ projected from point $L_1$ with the surface 104 of the object 106. Plane $P_1$ includes the light source $L_1$, the first point S (e.g., radiation source 112), point O and the principal axis SO. Likewise, the second light stripe projector 102 projects a plane of light onto the surface 102 of the object 104 from a point $L_2$ resulting in the light stripe $l_2$ being projected onto the surface 102. The light stripe $l_2$ is thus formed by the intersection of the plane of light $P_2$ projected from the point $L_2$ with the surface 102 of the object 104. Plane $P_2$ includes the light source $L_2$, the first point S (e.g., radiation source 112), point O and the principal axis SO.

The imaging device 110 detects the position of the second point O by sensing light of the intersecting light stripes $l_1$ and $l_2$ that is reflected by the surface 102 at the second point O on the surface 102. In exemplary embodiments, the imaging device 110 comprises a camera including a lens assembly 114 having a focal point F and a sensor 116 having a two-dimensional array of sensing elements 118. In exemplary embodiments, the sensor 116 may include sensing elements 118 comprised of charge coupled devices (CCDs), complimentary metal hydride oxide semiconductor (CMOS) devices, or the like. The camera may also be used for other purposes such as for acquiring images used before, during and after radiation therapy. For example, an imaging device 110 comprising a two-dimensional camera may be used to acquire images for verification and recordation of patient position and radiation field as well as source to skin distance (SSD).

In the embodiment illustrated, the system 100 further includes a distance calculator 120 for calculating the distance between the first point S and the second point O using the position of the second point O detected by the imaging device 110. In exemplary embodiments, the distance calculator 120 may be implemented as hardware, firmware or software in a dedicated controller or computer. For example, in one embodiment, the distance calculator 120 may be implemented as software executed by a computer integrated with a radiation treatment device, such as the radiation treatment device 400 shown in FIG. 6.

For purposes of discussion, the imaging device 110 may be modeled as a simple pinhole camera, which defines the basic projective imaging geometry with which three dimensional (3D) objects are projected onto a two dimensional (2D) image surface (i.e., the sensor 116 of the imaging device 110 (FIG. 1)). A pinhole camera may be described by a set of intrinsic and extrinsic parameters. The intrinsic parameters may be those that define the optical properties of the camera such as the focal length, the aspect ratio of the pixels, and the location of the image center where the optical axis intersects the image plane. Another intrinsic parameter may be the skew of the image plane axes. The extrinsic parameters may define the position and orientation (pose) of the camera with respect to some external world coordinate system. Thus, the position of an image of point O, the intersection of the principal axis SO and the surface 102 of the object 104, may be projected onto the sensor 116 by tracing a ray from point O through the focal point F until the ray intersects with one or more sensing elements 118 of the sensor 116 at the point O'. Thus, the point O' represents the projection of the second point O onto the sensor 116. Point O' may appear as a bright point on the sensor 116. The sensor 116 senses the position of this bright point, and thus the position of point O' allowing the position of the second point O to be determined.

Figure 2:
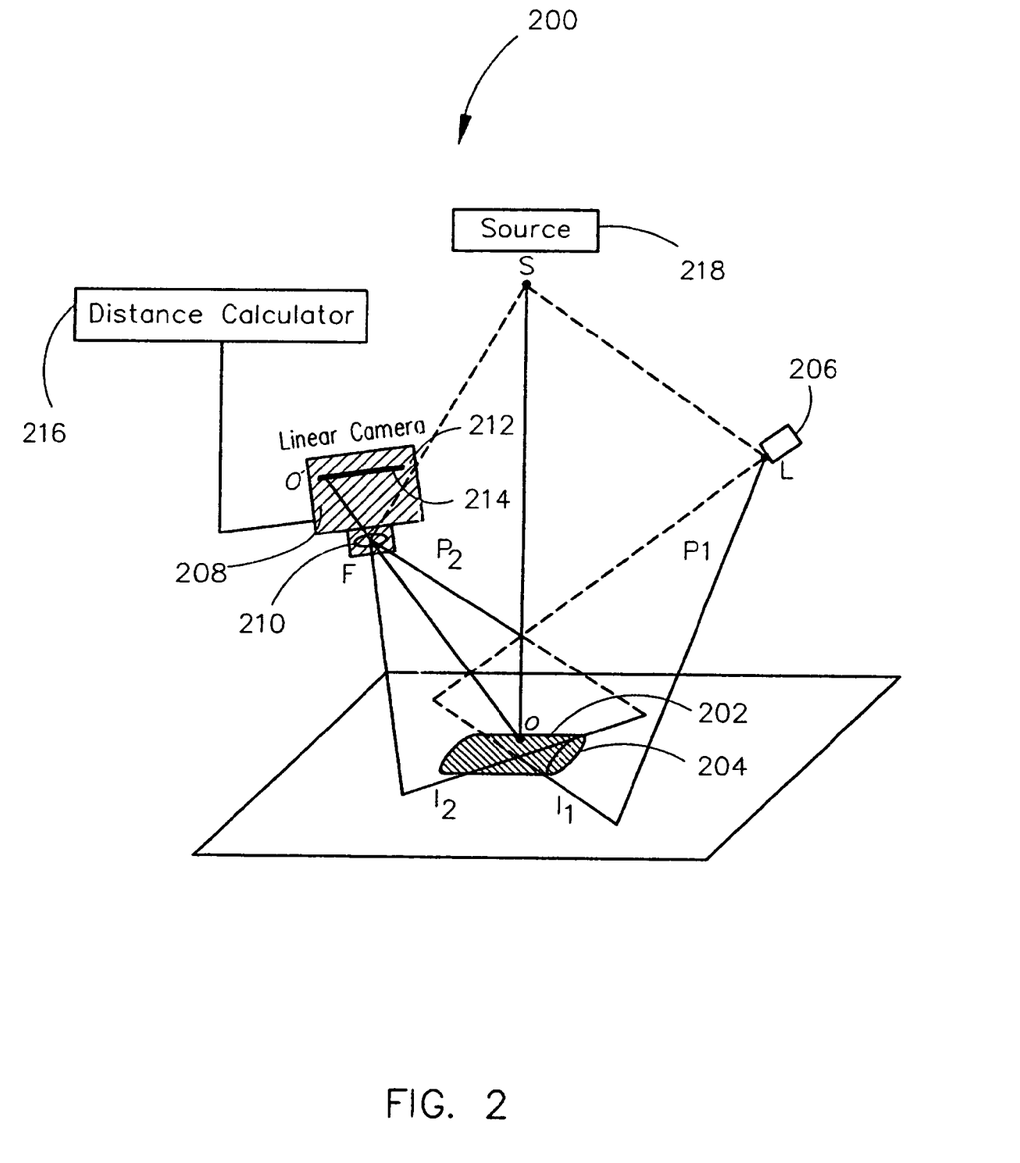
FIG. 2 is a block diagram illustrating a system for measuring the distance from a first point spaced away from a surface of the object to a second point on a surface of an object in accordance with a second exemplary embodiment of the present invention.

Turning now to FIG. 2, an alternative system 200 for measuring the distance from a first point S spaced away from a surface 202 of an object 204 to a second point O on the surface 202 along an axis passing through the first point S and the second point O is disclosed. As shown in FIG. 2, the system 200 includes a projection assembly 206 for projecting a sheet or plane of light onto the surface 202 of the object 204 so that the intersection of the plane of light with the surface 202 forms a light stripe $l_1$ on the surface 202. The projection assembly 206 may comprise a light stripe projector using a known light projection technology. For example, in exemplary embodiments, the projection assembly 206 may include a conventional light source coupled with a lens/mask system for projecting light in a plane. Laser or laser diode-based projection technologies may also be utilized. Light projected by the projection assembly 206 may be visible or invisible to the human eye (e.g., the light may have a wavelength in the visible range or may be ultraviolet, infrared, or the like) without departing from the scope and intent of the present invention.

An imaging device 208 detects the position of the second point O by sensing light of the light stripe that is reflected by the surface 202 at the second point O on the surface 202. In exemplary embodiments, the imaging device 208 comprises a linear (one-dimensional) camera having a lens assembly 210 having a focal point F and a linear sensor 212 having a linear array of sensing elements 214 oriented for sensing light reflected from points on the surface 202 of the object 204 along a line coplanar with the first point, the second point and the focal point of the imaging device 208. In exemplary embodiments, the linear sensor 212 may include sensing elements 214 comprised of charge coupled devices (CCDs), complimentary metal hydride oxide semiconductor (CMOS) devices, or the like. Alternatively, the imaging device 208 may be a two-dimensional camera having a sensor employing a two-dimensional array of sensing elements (e.g., CCDs, CMOS devices, or the like), wherein only one row or column of elements is utilized. In this manner, the imaging device may also be used for other purposes such as for acquiring images used before, during and after radiation therapy. For example, an imaging device 208 comprising a two-dimensional camera may be used to acquire images for verification and recordation of patient position and radiation field as well as source to skin distance (SSD).

The system 200 further includes a distance calculator 216 for calculating the distance between the first point S and the second point O using the position of the second point O detected by the imaging device 208. Again, the distance calculator 216 may be implemented as hardware, firmware or software in a dedicated controller or computer. For example, in one embodiment, the distance calculator 216 may be implemented as software executed by a computer integrated with a radiation treatment device, such as the radiation treatment device 300, shown in FIG. 6.

In FIG. 2, the line SO again represents the principle axis of the system 200, where point S is the first point and point O is the second point representing the intersection of the principle axis SO with the surface 202 of the object 204. The projection assembly 206 projects a plane of light onto the surface 202 of the object 206 from a point L resulting in a light stripe $l_1$ being projected onto the surface 202. The light stripe $l_1$ is thus formed by the intersection of the plane of light $P_1$ with the surface 202 of the object 204. Plane $P_1$ thus includes the light source L, the first point S (e.g., radiation source 218), the second point O and the principal axis SO.

Modeling the imaging device 208 as a simple pinhole camera, the linear sensor 212 may be viewed as being projected onto the surface 202 of the object 204 as line $l_2$. In this manner, a plane $P_2$ may be formed by the intersection of focal point F of the imaging device 208 and the principal axis SO. Plane $P_2$ thus includes the sensing elements 214 of the linear sensor 212 and the first point S (e.g., the radiation source 218). The principal axis SO is the intersection of planes $P_1$ and $P_2$.

The position of an image of point O, the intersection of the principal axis SO and the surface 202 of the object 204, may be projected onto the linear sensor 212 by tracing a ray from point O through the focal point F until the ray intersects with one or more sensor elements 214 of the linear sensor 212 at point O'. Point O' represents the projection of the second point O onto the linear sensor 212. Point O' comprises a bright point on the linear sensor 212. The linear sensor 212 senses the position of this bright point, and thus the position of point O' allowing the position of the second point O to be determined.

Figure 3:
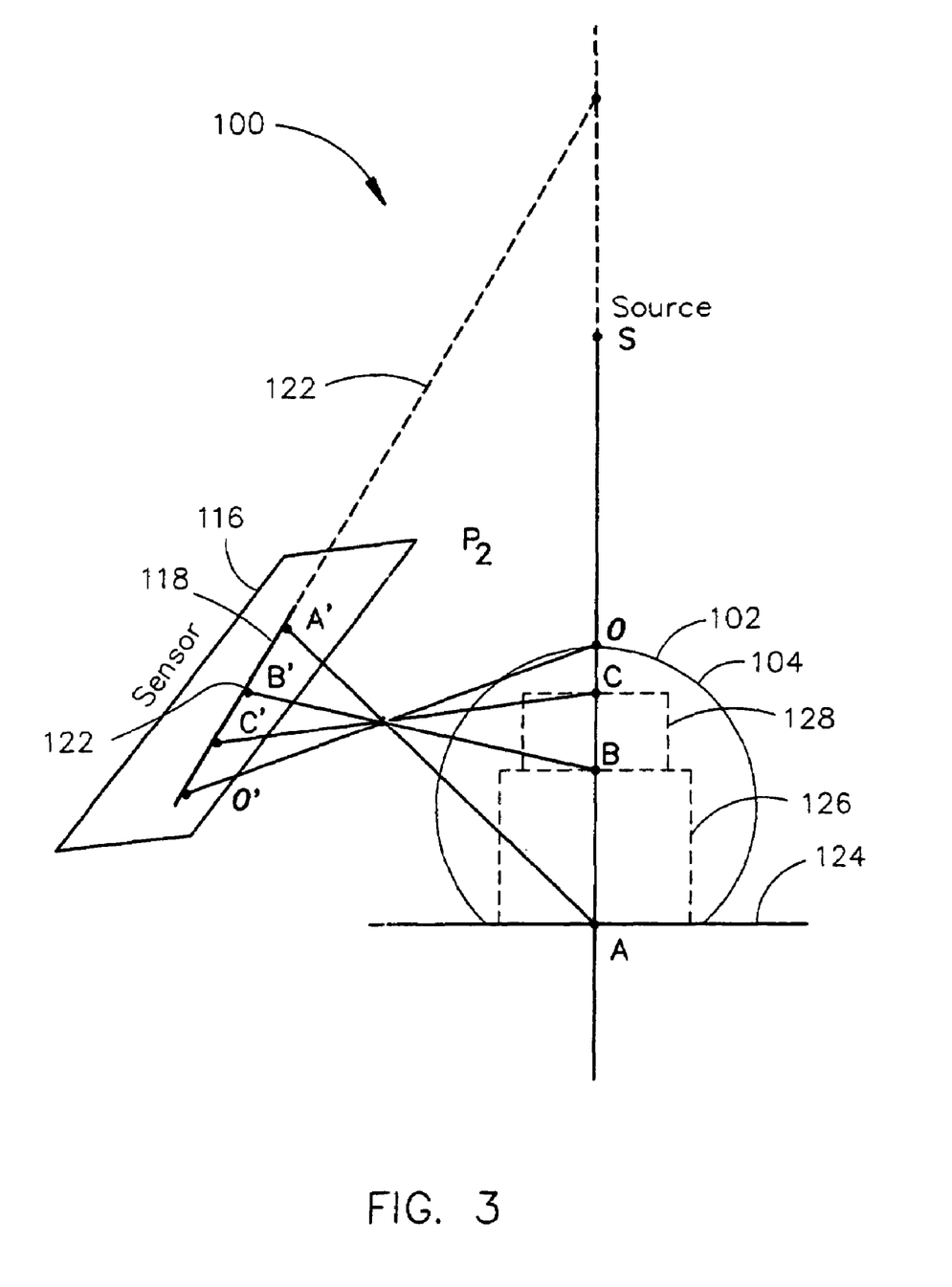
FIG. 3 is a block diagram illustrating calibration of the system shown in FIG. 1 for calculating the distance between the first point and the second point.
Figure 4:
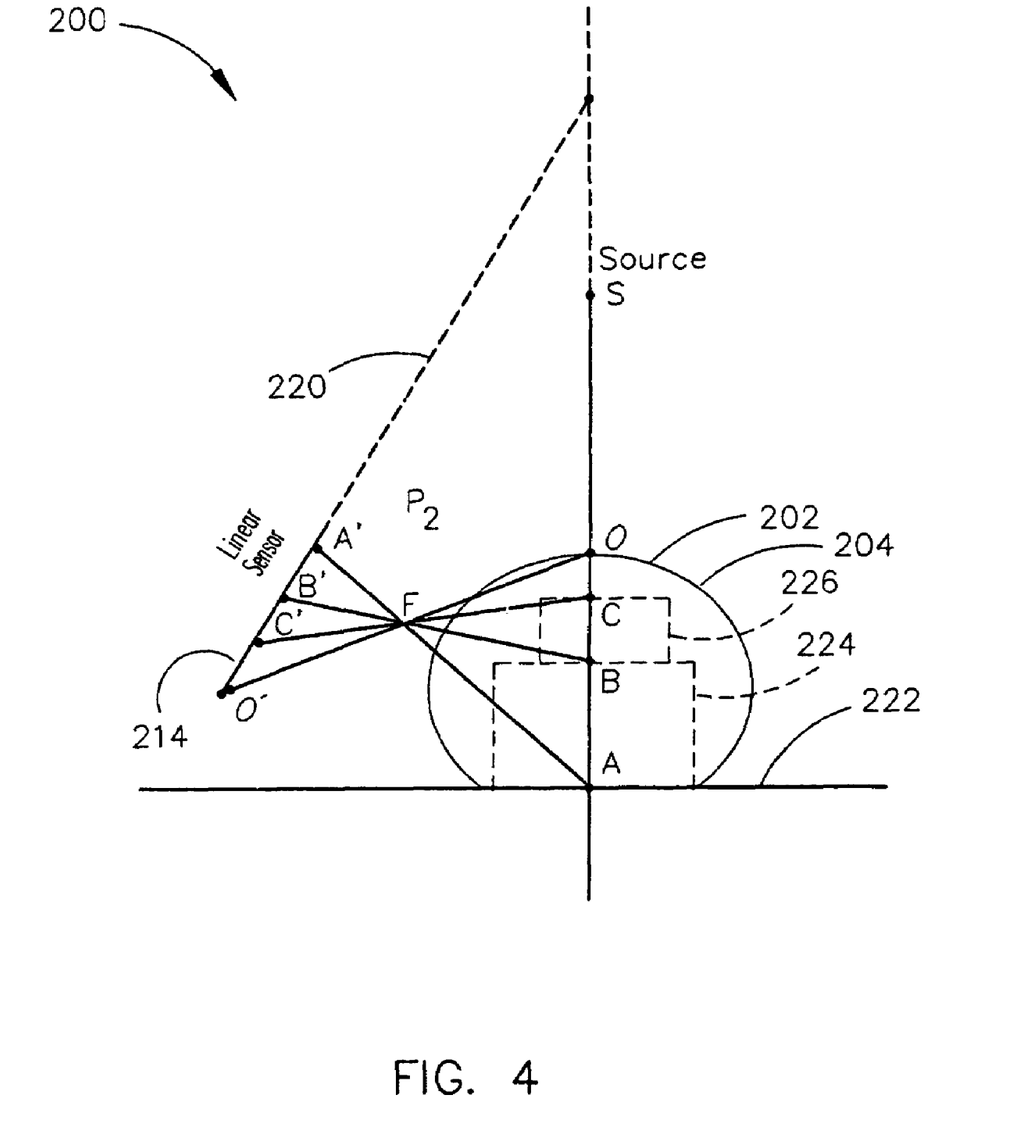
FIG. 4 is a block diagram illustrating calibration of the system shown in FIG. 2 for calculating the distance between the first point and the second point.

FIGS. 3 and 4 illustrate calibration of the systems 100 and 200 shown in FIGS. 1 and 2, respectively, for calculating the distance between the first point S and the second point O. As shown in FIG. 3, the principal axis SO and a line 122 of sensor elements 118 extending along the face of the sensor 116 are coplanar, both lying in plane $P_2$. Similarly, as shown in FIG. 4, the principal axis SO and the linear sensor line 220 extending along the face of the linear sensor 214 are coplanar, both lying in plane $P_2$. Three additional points: points A, B and C, may be defined on the principal axis SO. Using a pinhole camera model, points A, B, C and O may be projected onto the line 122 of sensor elements 118 (FIG. 3) or the linear sensor 214 (FIG. 4) through the focal point F. Thus, the projections A', B', C', and O' of those points, respectively, through focal point F onto the two-dimensional sensor 116 (FIG. 3), or the linear sensor 214 (FIG. 4) are located along lines 122 and 214, respectively.

The distance SA is predetermined and is thus known. For example, in an embodiment wherein the systems 100 or 200 is used as the range finder in a radiation treatment device 400 (see FIG. 6), point S may be the location of the radiation source or the emitter of the radiation treatment device and the third point A may be a point on a surface 124 or 222 beneath the emitter, such as the surface of a table on which the patient rests during treatment. Thus, the distance SA is measurable and, in exemplary embodiments, constant.

The fourth point B is located between points S and A on the principle axis SO. The distance AB is also predetermined and thus known. For example, in the embodiment wherein the systems 100 or 200 shown in FIGS. 1 and 2 are used as the range finder of a radiation treatment device, point B may be a point on the surface of a calibration object 126 or 224, such as a block of known height or thickness. The calibration object 126 or 224 may be placed on the surface 124 or 222 along the principle axis SO during calibration and removed during treatment. The height of the calibration object 126 or 224 is equal to distance AB and may be directly measured. Thus, the distance AB like the distance SA is known.

The fifth point C is located between points S and B on the principle axis SO. The distance AC, like the distances SA and AB, is predetermined and thus known. For example, in the embodiment wherein the systems 100 or 200 shown in FIGS. 1 and 2 are used as the range finder of a radiation treatment device, a second calibration object 128 or 226 may be placed onto the first calibration object 126 or 224. Point C is a point on the second calibration object 128 or 226 located along the principle axis SO. The height or thickness of the second calibration object 128 or 226 is equal to distance BC. Thus, the distance AC may be determined by adding the distances AB and BC. Alternatively, the second calibration object 128 or 226 may have a height or thickness equal to the distance AC. In this embodiment, the first calibration object 126 or 224 is removed from the surface 124 or 222 allowing the second calibration object 128 or 226 to be placed directly on the surface 124 or 222 instead of the first calibration object 126 or 224.

Calibration points A, B, and C may have projections A', B', and C' on the sensor line 122 (FIG. 3) or the linear sensor 114 (FIG. 4), allowing the sensor 116 or linear sensor 114 to be calibrated by locating the positions of projections A', B', and C' thereon and correlating the distances between projections A', B', and C' with the known distances between points A, B and C. When an object 104 or 204, such as the body of a patient, is placed on the surface 124 or 222, the position of point O (e.g., a bright spot targeting a tumor isocenter) located on the surface 102 or 202 of the object 104 or 204 along the principle axis SO may be determined allowing the distance SO to be calculated using a cross-ratio. For example, for the four points A, B, C and O and their projections A', B', C' and O', the cross-ratios are defined as:

$$CR(A, B, C, O) = \frac{\frac{AC}{BC}}{\frac{AO}{BO}} = \frac{AC \cdot BO}{AO \cdot BC} \text{ and }$$

$$CR'(A', B', C', O') = \frac{\frac{A'C'}{B'C'}}{\frac{A'O'}{B'O'}} = \frac{A'C' \cdot B'O'}{A'O' \cdot B'C'}$$

Because it is known from perspective geometry that a cross-ratio is an invariant under perspective projection, the cross ratio of points A, B, C, and O is equal to the cross ratio of points A', B', C', and O'. Thus, $$CR(A, B, C, O) = CR'(A', B', C', O'),$$

or:

$$\frac{AC \cdot BO}{AO \cdot BC} = \frac{A'C' \cdot B'O'}{A'O' \cdot B'C'}$$

Points A, B, and C, as well as their projections A', B', and C' are known. As discussed, this may be achieved by presenting the system with calibration points A, B, and C, where the distances AB and AC are known. The projections A', B', and C' of points A, B, and C, may be measured from the sensor 116 (FIG. 3) or the linear sensor 214 (FIG. 4) and stored. The position of the second point O, and its respective projection O', may be measured or read from sensor 116 or the linear sensor 214. Accordingly, the distance AO may be determined from:

$$AO = \frac{AC \cdot BO \cdot A'C' \cdot B'O'}{BC \cdot A'C' \cdot BO} = \frac{AC \cdot (AO - AB) \cdot A'O' \cdot B'C'}{BC \cdot A'C' \cdot B'O'}$$

or:

$$AO = \frac{AC \cdot AB \cdot A'O' \cdot B'C'}{(AC \cdot A'O' \cdot B'C') - (BC \cdot A'C' \cdot B'O')}$$

Distance SO, the distance from the first point to the second point (e.g., the distance from the source to the object), may be calculated by subtracting the distance AO from the distance SA:

$$SO = SA - AO$$

since the distance SA is known. Therefore, the distance SO may be calculated from:

$$SO = SA - \left( \frac{AC \cdot AB \cdot A'O' \cdot B'C'}{(AC \cdot A'O' \cdot B'C') - (BC \cdot A'C' \cdot B'O')} \right)$$

In the systems shown in FIGS. 1 and 2, this calculation is performed by the distance calculator 120 or 216 using inputs measured by the imaging devices 110 or 208, respectively.

Figure 5A:
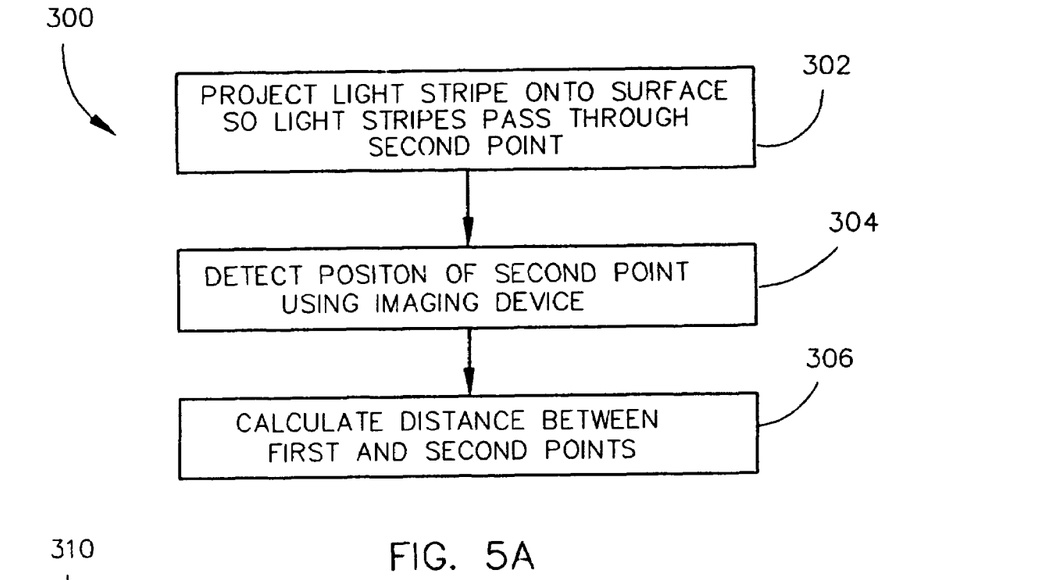
FIG. 5A is a flow diagram illustrating an exemplary method suitable for use by the system shown in FIGS. 1 and 2 for measuring the distance from the first point to the point.

Referring now to FIGS. 5A and 5B, exemplary methods 300 and 310 suitable for use by the system 100 shown in FIG. 1 or the system 200 shown in FIG. 2 for measuring the distance from the first point S to the second point O is described. As shown in FIG. 5A, the method 300 includes the steps of projecting light stripes onto the surface of an object, at step 302, so that one or more of the light stripes pass through the second point, detecting the position of the second using the imaging device, at step 304, calculating the distance between the first and second points using the detected position of the second point, at step 306. For instance, using the system 100 shown in FIG. 1, two or more light stripes are projected onto the surface 102 of the object 104, at step 302, so that the light stripes intersect at the second point O located on the surface 102 of the object 104. For example, in the specific embodiment illustrated, first and second planes of light $P_1$ and $P_2$ are projected, at step 302, so that the planes of light $P_1$ and $P_2$ intersect the surface 102 of the object 104 to form intersecting first and second light stripes $l_1$ and $l_1$ on the surface 102. The position of the second point O is then detected, at step 304, by using the two-dimensional image detector 110 to sense the position of the intersection of the light stripes $l_1$ and $l_2$. The distance between the first point S and the second point O may then be calculated, at step 306, for example, by the distance calculator 120, using the position of the second point O detected at step 304. Similarly, using the system 200 shown in FIG. 2, a light stripes $l_1$ is projected onto the surface 202 of the object 204, at step 302, so that the light stripe passes though the second point O located on the surface 202. The position of the second point O is then detected, at step 304 by using the linear sensor 212 of the imaging device 208 to sense the position of the light stripe at the second point O. As in the first embodiment, the distance between the first point S and the second point O may then be calculated, at step 306, using the position of the second point O detected at step 304.

Figure 5B:
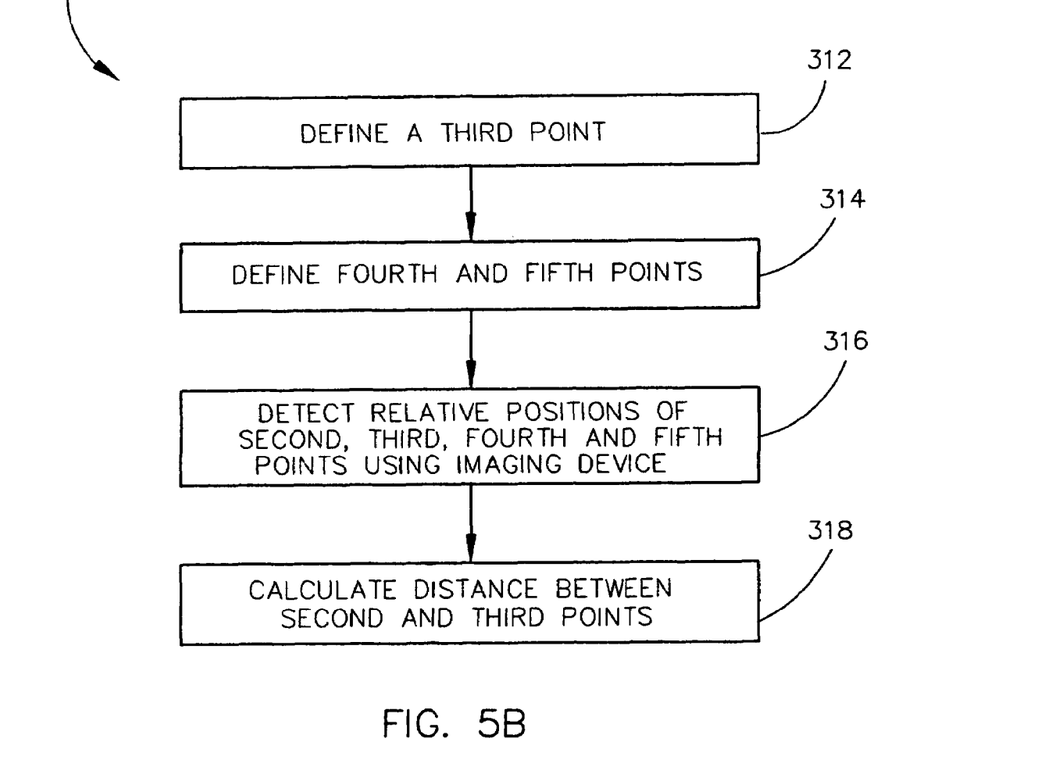
FIG. 5B is a flow diagram illustrating an exemplary method for calibrating the systems shown in FIGS. 1 and 2.

As shown in FIG. 5B, with reference to FIGS. 3 and 4, the system is calibrated, using method 310, for calculating the distance between the first point S and the second point (i.e., distance SO) along the principle axis. A third point, point A, may be defined along the principle axis, at step 312. The distance between the first point S and the third point A is predetermined and thus known. The distance between the second point O and third point A may be defined, at steps 314-318, using perspective geometry. For example, in exemplary embodiments, a fourth point B and a fifth point C may be defined along the principle axis, at step 314. The distance between the first point S and the third point A (distance SA) is greater than the distance between the first point S and the fourth point B (distance SB). Similarly, the distance between the first point S and the fourth point B (distance SB) is greater than the distance between the first point A and the fifth point C (distance SC). The relative positions of the second point O, the third point A, the fourth point B and the fifth point C may be detected, at step 316, using the two-dimensional imaging device 110 shown in FIG. 1 or the linear imaging device 208 shown in FIG. 2. The distance between the third point A and the fifth point C (distance AC) is predetermined. The distance between the second point O and the third point A (distance AO) may be calculated, at step 318, using the distance between the third point A and the fourth point B (distance AB), and the distance between the third point A and the fifth point C (distance AC), which are know using the cross ratios of the points A, B, C and O and the projections A', B', C' and O' of these points on the sensor 116 or 214. The distance between the second point O and the third point A (distance AO) may then be subtracted from the distance between the first point S and the third point A (distance SA) to determine the distance between the first point S and the second point O (distance SO), i.e., the source to object distance.

In exemplary embodiments, the methods 300 and 310 may be implemented as computer-executable instructions (e.g., software, firmware, or the like) and may be stored in a computer-readable medium and executed by a computer, the control system of a radiation treatment device such as a linear accelerator (LINAC), a range finder system, or the like. It is understood that the specific order or hierarchies of steps in the methods disclosed are examples of exemplary approaches. Based upon design preferences, it is understood that the specific order or hierarchy of steps in the method can be rearranged while remaining within the scope of the present invention. The attached method claims present elements of the various steps in a sample order, and are not meant to be limited to the specific order or hierarchy presented.

Figure 6:
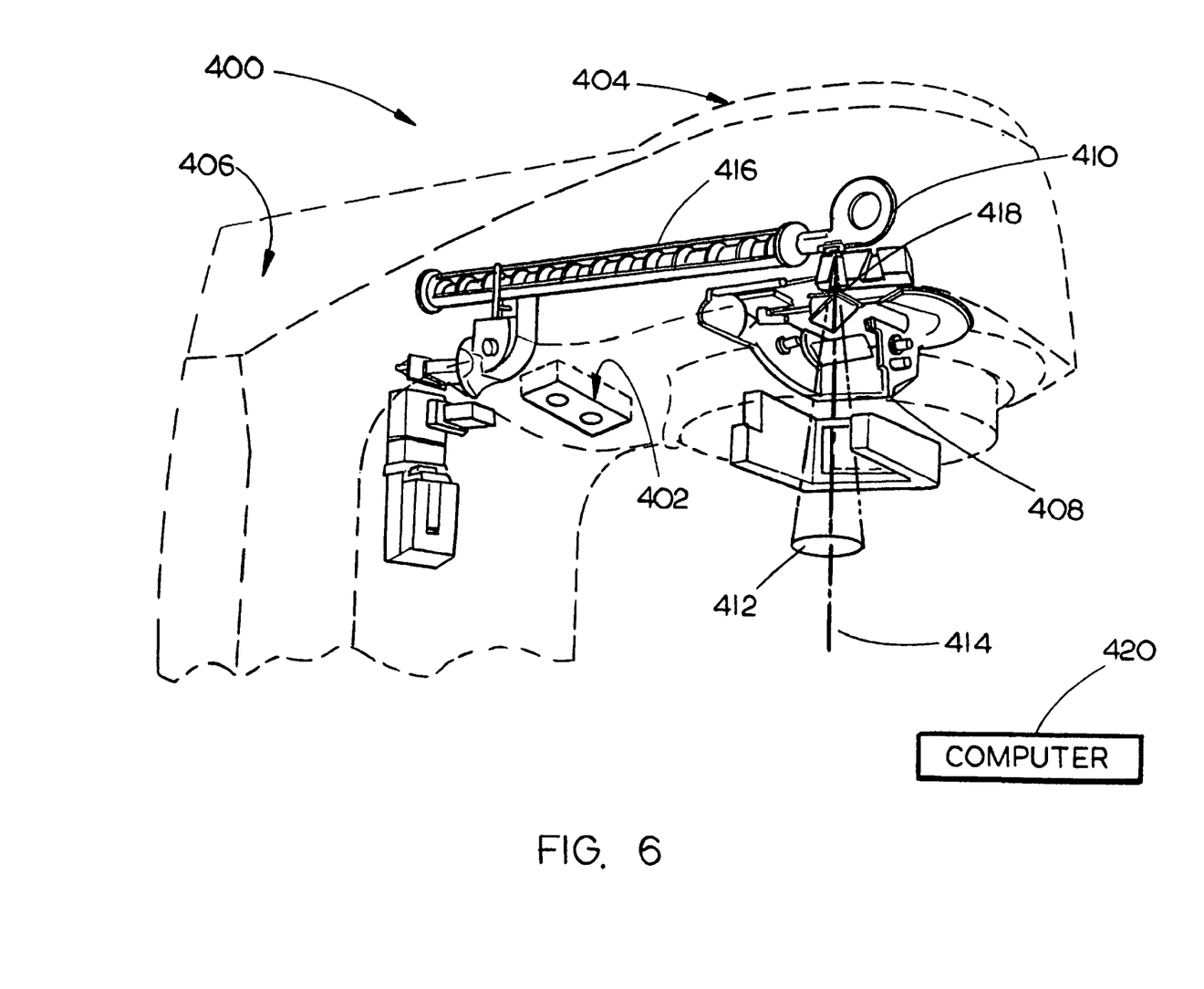
FIG. 6 is an isometric view illustrating an exemplary radiation treatment device employing a remote center range finder in accordance with the present invention for measuring the distance from the radiation source of the radiation treatment device to a second point on the surface of the patient's body along the principle axis of the device (i.e., the SSD).

In one specific embodiment, the systems 100 and 200 illustrated in FIGS. 1 and 2 may be used in a radiation treatment device as a range finder for determining the source-to-skin-distance (SSD). Accordingly, FIG. 6 illustrates a radiation treatment device 400 employing a remote center range finder 402 implementing one or both of the systems shown in FIGS. 1 through 4 in accordance with an exemplary embodiment of the present invention. The radiation treatment device 400 includes a protective cabinet 404 primarily comprised of a gantry 406 supporting a treatment head 408 housing a radiation source 410. The radiation source 410 may irradiate at least one field of the body of a patient with therapeutic radiation in the form of an output radiation beam 412 along the principle axis 414. The radiation beam 412 may comprise an electron beam, a photon beam, gamma radiation, X-ray radiation, or any other type of radiation having particular therapeutic benefits in the treatment of the patient. In exemplary embodiments, the radiation source 410 comprises an electron accelerator such as a linear accelerator (LINAC) 416, or the like, for generating and emitting the therapeutic radiation. During treatment, the radiation beam 412 may be trained on a zone or area of the body of the patient who is to be treated, and who may lie on a table at the isocenter of the gantry rotation. The gantry 406 may then be swiveled around a horizontal axis of rotation in the course of therapeutic treatment so as to provide different beam angles and radiation distributions with respect to the patient. The treatment head 408 includes a beam emitting device or emitter 418 for emitting the radiation beam 412, which may be used during calibration, verification, and/or treatment. The rotational axis of the gantry 406, the rotational axis of a treatment table and the radiation beam axis (e.g., principle axis 414) all preferably intersect in an isocenter of the radiation treatment device 400. A computer or controller 420 controls various aspects of the radiation treatment and receives patient information. The computer 420, which may in exemplary embodiments be a LINAC computer, is typically operated by a therapist or like operator who is located in a different room than the patient to be treated, so as to be protected from radiation, and is therefore shown in FIG. 6 in block form.

In accordance with the present invention, the remote center range finder 402 directly measures the source-to-skin-distance (SSD) during radiation treatment by directly measuring the distance of the radiation source, specifically, the emitter 418, to a point on the body of the patient where the body is intersected by the principle axis 414. By directly measuring SSD, the remote center range finder 402 provides highly accurate and precise SSD measurements, allowing for the use of more aggressive treatment plans specifying higher doses or larger beam shapes than would be possible with less accurate SSD measurements.

It will be appreciated that the systems 100 and 200, and methods 300 and 310 described in the discussion of FIGS. 1 through 5B, are not limited to application as a remote center range finder 402 as shown in FIG. 6. Instead, it is contemplated that the systems 100 and 200 and methods 300 and 310 may be used in virtually any application where it is desirable to obtain an accurate measurement of the distance from a first point spaced away from a surface of an object to a second point on the surface of an object. Such applications may include medical diagnostic and/or treatment applications, manufacturing applications, object inspection applications, and the like.

It is believed that the present invention and many of its attendant advantages will be understood by the foregoing description, and it will be apparent that various changes may be made in the form, construction and arrangement of the components thereof without departing from the scope and spirit of the invention or without sacrificing all of its material advantages. The form herein before described being merely an explanatory embodiment thereof, it is the intention of the following claims to encompass and include such changes.

What is claimed:

1. A system for measuring the distance from a first point spaced away from a surface of an object to a second point on a surface of an object along an axis extending through the first point and the second point, comprising:
   a first projection assembly for projecting a first plane of light so that the first plane of light contains the second point and intersects the surface of the object to form a first light stripe on the surface;
   a second projection assembly for projecting a second plane of light so that the second plane of light contains the second point and intersects the surface of the object to form a second light stripe on the surface, the first light stripe intersecting the second light stripe at the second point;
   an imaging device for detecting the position of the second point by sensing the intersection of the first light stripe and the second light stripe at the second point; and
   a distance calculator for calculating the distance between the first point and the second point along the axis using the position of the second point detected by the imaging device,
   wherein the distance between the first point and the second point is determined from the detected position of the second point and the imaging device detects the position of a third point along the axis, the distance between the first point and the third point being predetermined, and wherein the distance calculator determines the distance between the second point and the third point and subtracts the distance between the second point and the third point from the distance between the first point and the third point for determining the distance between the first point and the second point.

2. The system as claimed in claim 1, wherein the imaging device detects the position of a fourth point and a fifth point along the axis, the distance between the third point and the fourth point and the distance between the third point and the fifth point being predetermined and the distance between the first point and the third point being greater than the distance between the first point and the fourth point, and the distance between the first point and the fourth point being greater than the distance between the first point and the fifth point, and wherein the distance calculator calculates the distance between the second point and the third point using the distance between the third point and the fourth point and distance between the third point and the fifth point.

3. The system as claimed in claim 2, wherein the second, third, fourth and fifth points are projected onto the sensor and the distance between the second point and the third point is determined using the cross-ratio of the second, third, fourth and fifth points and the projections of the second, third, fourth, and fifth points onto the sensor.

4. The system as claimed in claim 3, wherein the distance between first point and the second point is calculated from the equation $$SO = SA - \left( \frac{AC \cdot AB \cdot A'O' \cdot B'C'}{(AC \cdot A'O' \cdot B'C') - (BC \cdot A'C' \cdot B'O')} \right)$$

where S is the first point, O is the second point, A is the third point, B is the fourth point, C if the fifth point, O' is the projection of the second point on the sensor, A' is the projection of the third point on the sensor, B' is the projection of the fourth point on the sensor; C' is the projection of the fifth point on the sensor, SO is the distance between S and O, SA is the distance between A and S, AB is the distance between A and B, AC is the distance between A and C; BC is the distance between B and C determined by subtracting AB from AC, A' C' is the distance between A' and C', A'O' is the distance between A' and O', B'C' is the distance between B' and C' and B'O' is the distance between B' and O'.

5. The system as claimed in claim 4, wherein A'C', A'O', B'C', and B'O' are measured from the sensor.

6. The system as claimed in claim 5, wherein the sensor comprises a two-dimensional array of light sensing elements.

7. A radiation treatment device, comprising:
a radiation source for projecting a beam of radiation onto a body of a patient being treated; and
a range finder for measuring a distance from the radiation source to a second point on the surface of the body of the patient being treated along an axis extending through the radiation source and the second point, the range finder including:
  a first projection assembly for projecting a first plane of light so that the first plane of light intersects the surface of the body to form a first light stripe on the surface; and
  a second projection assembly for projecting a second plane of light so that the second plane of light intersects the surface of the body to form a second light stripe on the surface, the first light stripe intersecting the second light stripe at the second point;
  an imaging device for detecting the position of the second point by sensing the intersection of the first light stripe and the second light stripe at the second points; and
  a distance calculator for calculating the distance between the radiation source and the second point using the position of the second point detected by the imaging device,
  wherein the distance between the first point and the second point is determined from the detected position of the second point and the imaging device detects the position of a third point along the axis, the distance between the radiation source and the third point being predetermined, and the distance calculator determines the distance between the second point and the third point and subtracts the distance between the second point and the third point from the distance between the radiation source and the third point for determining the distance between the radiation source and the second point.

8. The radiation treatment device as claimed in claim 7, wherein the imaging device detects the position of a fourth point and a fifth point along the axis, the distance between the third point and the fourth point and the distance between the third point and the fifth point being predetermined and the distance between the radiation source and the third point being greater than the distance between the radiation source and the fourth point, and the distance between the radiation source and the fourth point being greater than the distance between the radiation source and the fifth point; and wherein the distance calculator calculates the distance between the second point and the third point using the distance between the third point and the fourth point and distance between the third point and the fifth point.

9. The radiation treatment device as claimed in claim 8, wherein the second, third, fourth and fifth points are projected onto the sensor and the distance between the second point and the third point is determined using the cross-ratio of the second, third, fourth and fifth points and the projections of the second, third, fourth, and fifth points onto the sensor.

10. The radiation treatment device as claimed in claim 9, wherein he distance between radiation source and the second point is calculated from the equation $$SO = SA - \left( \frac{AC \cdot AB \cdot A'O' \cdot B'C'}{(AC \cdot A'O' \cdot B'C') - (BC \cdot A'C' \cdot B'O')} \right)$$

where S is the first point, O is the second point, A is the third point, B is the fourth point, C if the fifth point, O' is the projection of the second point on the sensor, A' is the projection of the third point on the sensor, B' is the projection of the fourth point on the sensor; C' is the projection of the fifth point on the sensor, SO is the distance between S and O, SA is the distance between A and S, AB is the distance between A and B, AC is the distance between A and C; BC is the distance between B and C determined by subtracting AB from AC, A' C' is the distance between A' and C', A'O' is the distance between A' and O', B'C' is the distance between B' and C' and B'O' is the distance between B' and O'.

11. The radiation treatment device as claimed in claim 10, wherein A'C', A'O', B'C', and B'O' are measured from the sensor.

12. A method for measuring a distance from a first point spaced away from a surface of an object to a second point on a surface of an object along an axis extending through the first point and the second point, comprising:
projecting a first plane of light so that the first plane of light intersects the surface of the object to form a first light stripe on the surface;
projecting a second plane of light so that the second plane of light intersects the surface of the object to form a second light stripe on the surface, the first light stripe intersecting the second light stripe at the second point; and detecting the position of the second point by sensing the intersection of the first light stripe and the second light stripe at the second point, the distance between the first point and the second point being determined from the detected position of the second point;

defining a third point along the axis, the distance between the first point and the third point being predetermined;

determining the distance between the second point and the third point; and subtracting the distance between the second point and the third point from the distance between the first point and the third point for determining the distance between the first point and the second point.

13. The method as claimed in claim 12, wherein determining the distance between the second point and the third point comprises:

defining a fourth point and a fifth point along the axis, the distance between the first point and the third point being greater than the distance between the first point and the fourth point, and the distance between the first point and the fourth point being greater than the distance between the first point and the fifth point;

detecting the relative positions of the second point, the third point, the fourth point and the fifth point using the imaging device, the distance between the third point and the fourth point and the distance between the third point and the fifth point being predetermined; and calculating the distance between the second point and the third point using the distances between the third point and the fourth point and the third point and the fifth point.

14. The method as claimed in claim 13, wherein the distance between the second point and the third point is determined using the cross-ratio of the second, third, fourth and fifth points and the projections of the second, third, fourth, and fifth points on the sensor.

15. The method as claimed in claim 14, wherein the distance between first point and the second point is calculated from the equation $$SO = SA - \left( \frac{AC \cdot AB \cdot A'O' \cdot B'C'}{(AC \cdot A'O' \cdot B'C') - (BC \cdot A'C' \cdot B'O')} \right)$$

where S is the first point, O is the second point, A is the third point, B is the fourth point, C if the fifth point, O' is the projection of the second point on the sensor, A' is the projection of the third point on the sensor, B' is the projection of the fourth point on the sensor; C' is the projection of the fifth point on the sensor, SO is the distance between S and O, SA is the distance between A and S, AB is the distance between A and B, AC is the distance between A and C, BC is the distance between B and C determined by subtracting AB from AC, A' C' is the distance between A' and C', A'O' is the distance between A' and O', B'C' is the distance between B' and C'and B'O' is the distance between B' and O'.

16. The method as claimed in claim 15, wherein A'C', A'O', B'C', and B'O' are measured from the sensor.

* * * * *